(12) United States Patent
Zeng et al.

(10) Patent No.: US 12,390,500 B2
(45) Date of Patent: Aug. 19, 2025

(54) PHARMACEUTICAL COMPOSITION OF A RECOMBINANT ADENO-ASSOCIATED VIRUS VECTOR AND ITS APPLICATION

(71) Applicant: Sichuan Real&Best Biotech Co., Ltd., Sichuan (CN)

(72) Inventors: Yi Zeng, Sichuan (CN); Jialing Jiang, Sichuan (CN)

(73) Assignee: Sichuan Real & Best Biotech Co., Ltd., Sichuan (CN)

( * ) Notice: Subject to any disclaimer, the term of this patent is extended or adjusted under 35 U.S.C. 154(b) by 0 days.

(21) Appl. No.: 18/515,559

(22) Filed: Nov. 21, 2023

(65) Prior Publication Data
US 2024/0165177 A1    May 23, 2024

(30) Foreign Application Priority Data
Nov. 22, 2022   (CN) .......................... 202211467932.8

(51) Int. Cl.
     *A61K 35/768*      (2015.01)
     *A61K 47/02*      (2006.01)
     (Continued)

(52) U.S. Cl.
     CPC ............ *A61K 35/768* (2013.01); *A61K 47/02* (2013.01); *A61K 47/10* (2013.01); *A61K 47/18* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 2005/0186225 A1* | 8/2005 | Evans | A61K 9/0019 424/233.1 |
| 2014/0348876 A1 | 11/2014 | Jezek et al. | |

(Continued)

FOREIGN PATENT DOCUMENTS

| | | |
|---|---|---|
| CN | 102205132 A | 10/2011 |
| CN | 112352050 A | 2/2021 |

(Continued)

OTHER PUBLICATIONS

The extended European search report mailed Apr. 10, 2024 in corresponding European Patent Application No. 23211247.4 (9 pages).

(Continued)

*Primary Examiner* — David W Berke-Schlessel
(74) *Attorney, Agent, or Firm* — Rothwell, Figg, Ernst & Manbeck, P.C.

(57) ABSTRACT

The present invention belongs to the field of formulation of a recombinant adeno-associated virus vector, in particular relating to a pharmaceutical composition of a recombinant adeno-associated virus vector, comprising a recombinant adeno-associated virus (rAAV), an ion salt, a buffering agent, a stabilizer, and a surfactant, and its use. The rAAV vector carries hFIX and can be used to treat hemophilia B. The pharmaceutical composition can be stored at a refrigeration temperature, such as 2-8° C., for more than 1 year, maintain stable for such as genome titer and biological activity, and also has good stability when stored at room temperature for two weeks.

12 Claims, 5 Drawing Sheets

| Detection item | | Acceptable standard | 0 Mon | 1 Mon | 2 Mon | 3 Mon | 6 Mon | 9 Mon | 12 Mon |
|---|---|---|---|---|---|---|---|---|---|
| Exterior | | Should be colorless clear liquid | meets the regulations | meets the regulations | meets the regulations | meets the regulations | meets the regulations | meets the regulations | meets the regulations |
| Clarity | | Not thicker than No. 3 turbidity standard solution | meets the regulations | meets the regulations | meets the regulations | meets the regulations | meets the regulations | meets the regulations | meets the regulations |
| Visible foreign matter | | Meets the regulations | meets the regulations | meets the regulations | meets the regulations | meets the regulations | meets the regulations | meets the regulations | meets the regulations |
| Poloxamer 188 (μg/ml) | | 30-150μg/ml | 90.6 | 94.0 | 79.6 | 76.7 | 80.4 | 72.0 | 79.2 |
| Osmolality (mOsmol/kg) | | 330-410 mOsmol/kg | 368 | N/A | N/A | N/A | 366 | N/A | N/A |
| Capacity (ml) | | Should not be less than the marked capacity | meets the regulations | N/A | N/A | N/A | meets the regulations | N/A | N/A |
| Purity (SDS-PAGE) | | The total purity of capsid protein should not be less than 95% | 100.0 | 100.0 | 100.0 | 100.0 | 100.00 | 100.1 | 100.0 |
| Purity (SEC-HPLC, %) | | Monomer purity should not be less than 95% | 98.0 | 97.4 | 96.1 | 96.0 | 99.5 | 98.6 | 99.9 |
| pH | | 7.7-8.3 | 7.8 | 7.8 | 7.9 | 7.9 | 7.9 | 7.8 | 7.8 |
| Number of viral particles (vp/ml) | | $4.0 \times 10^{12} \sim 9.0 \times 10^{12}$ vp/ml | $6.60 \times 10^{12}$ | $7.02 \times 10^{12}$ | $6.14 \times 10^{12}$ | $6.05 \times 10^{12}$ | $7.38 \times 10^{12}$ | $7.34 \times 10^{12}$ | $5.72 \times 10^{12}$ |
| Genome titer (vg/ml) | | $1.5 \times 10^{12} \sim 4.5 \times 10^{12}$ vg/ml | $2.81 \times 10^{12}$ | $2.85 \times 10^{12}$ | $2.69 \times 10^{12}$ | $3.08 \times 10^{12}$ | $3.00 \times 10^{12}$ | $2.67 \times 10^{12}$ | $2.60 \times 10^{12}$ |
| Activity in vitro | Relative activity (%) | Relative activity and relative content should be 50%~150% | 115.15 | 78.26 | 113.51 | 114.71 | 123.81 | 105.88 | 131.25 |
| | Relative content (%) | | 119.26 | 87.05 | 118.62 | 109.68 | 114.62 | 117.01 | 118.05 |

(51) Int. Cl.
*A61K 47/10* (2017.01)
*A61K 47/18* (2017.01)
*A61K 47/26* (2006.01)

(56) References Cited

U.S. PATENT DOCUMENTS

| | | |
|---|---|---|
| 2017/0087219 A1 | 3/2017 | Bunting et al. |
| 2018/0140721 A1* | 5/2018 | Schauer ................. C07K 14/47 |
| 2018/0214379 A1 | 8/2018 | Bourles et al. |
| 2019/0070271 A1* | 3/2019 | Nathwani ...... C12Y 304/21022 |
| 2021/0163990 A1 | 6/2021 | Fritscher et al. |
| 2021/0317474 A1 | 10/2021 | Kaspar et al. |
| 2022/0119843 A1* | 4/2022 | Dai ...................... C12N 5/0601 |
| 2022/0136073 A1 | 5/2022 | Jiang et al. |
| 2022/0288233 A1 | 9/2022 | Wang et al. |
| 2022/0339297 A1 | 10/2022 | Schmidt et al. |
| 2023/0076072 A1* | 3/2023 | Karpes ................... A61P 43/00 |
| 2023/0364206 A1* | 11/2023 | Ohnsman ............... C12N 15/86 |
| 2023/0372538 A1* | 11/2023 | Bee .................... A61K 48/0091 |
| 2023/0414788 A1* | 12/2023 | Bee ...................... A61K 9/0024 |

FOREIGN PATENT DOCUMENTS

| | | |
|---|---|---|
| CN | 112575008 A | 3/2021 |
| CN | 114277057 A | 4/2022 |
| CN | 114617972 A | 6/2022 |
| CN | 114728049 A | 7/2022 |
| CN | 115337408 A | 11/2022 |
| WO | 2019/168961 A1 | 9/2019 |
| WO | 2021/071835 A1 | 4/2021 |
| WO | 2021/163322 A1 | 8/2021 |
| WO | 2022/133324 A1 | 6/2022 |
| WO | 2022/208342 A1 | 10/2022 |

OTHER PUBLICATIONS

Rambhai, et al., "Role of Essential Metal Ions in AAV Vector-Mediated Transduction", Molecular Therapy, Methods & Clinical Development, vol. 18, pp. 159-166, Sep. 2020 (8 pages).

Notice of Review Opinion mailed Aug. 30, 2024 in corresponding Taiwanese Patent Application No. 112136227 (with English machine translation)(17 pages).

* cited by examiner

| Examples | Conditions | Appearance | pH | Osmotic pressure (mOsm/L) | qPCR (vg/ml) | SEC-HPLC (%) | 5μm insoluble particles (Cumulative Counts/ml) | 10μm insoluble particles (Cumulative Counts/ml) | 25μm insoluble particles (Cumulative Counts/ml) | in vitro activity hFIX expression (ng/ml) |
|---|---|---|---|---|---|---|---|---|---|---|
| 1 | $T_0$ | colorless clear liquid | 7.62 | 375 | $8.48 \times 10^{11}$ | 95.9 | 82.5 | 12.5 | 0.0 | 38.6 |
| | Freeze and thaw 10 times | colorless clear liquid | 7.63 | | $5.81 \times 10^{11}$ | 95.7 | 215.0 | 10.0 | 0.0 | 30.2 |
| | 40°C, 7days (illumination:4500±500Lux) | colorless clear liquid | 7.61 | | $6.57 \times 10^{11}$ | 96.1 | 100.0 | 25.0 | 0.0 | 23.8 |
| 2 | $T_0$ | colorless clear liquid | 8.16 | 370 | $9.96 \times 10^{11}$ | 95.8 | 195.0 | 12.5 | 0.0 | 38.3 |
| | Freeze and thaw 10 times | colorless clear liquid | 8.18 | | $6.87 \times 10^{11}$ | 96.3 | 217.5 | 15.0 | 0.0 | 32.9 |
| | 40°C, 7days (illumination:4500±500Lux) | colorless clear liquid | 8.18 | | $8.15 \times 10^{11}$ | 95.5 | 105.0 | 0.0 | 0.0 | 30.3 |
| 3 | $T_0$ | colorless clear liquid | 8.59 | 367 | $8.04 \times 10^{11}$ | 95.4 | 172.5 | 2.5 | 0.0 | 35.7 |
| | Freeze and thaw 10 times | colorless clear liquid | 8.58 | | $8.57 \times 10^{11}$ | 94.9 | 142.5 | 10.0 | 0.0 | 30.1 |
| | 40°C, 7days (illumination:4500±500Lux) | colorless clear liquid | 8.63 | | $1.04 \times 10^{12}$ | 95.6 | 45.0 | 5.0 | 0.0 | 23.2 |

FIG. 1A

| Examples | Conditions | Appearance | pH | Osmotic pressure (mOsm/L) | qPCR (vg/ml) | SEC-HPLC (%) | 5μm insoluble particles (Cumulative Counts/ml) | 10μm insoluble particles (Cumulative Counts/ml) | 25μm insoluble particles (Cumulative Counts/ml) | in vitro activity hFIX expression (ng/ml) |
|---|---|---|---|---|---|---|---|---|---|---|
| 4 | T$_0$ | colorless clear liquid | 8.24 | 366 | 9.79×10$^{11}$ | 96.0 | 17.5 | 5.0 | 0.0 | 36.2 |
| | Freeze and thaw 10 times | colorless clear liquid | 8.28 | | 1.01×10$^{12}$ | 95.3 | 115.0 | 7.5 | 0.0 | 28.3 |
| | 40°C, 7days (illumination: 4500±500Lux) | colorless clear liquid | 8.27 | | 9.38×10$^{11}$ | 95.9 | 182.5 | 2.5 | 0.0 | 23.6 |
| 5 | T$_0$ | colorless clear liquid | 6.35 | 373 | 8.23×10$^{11}$ | 97.7 | N/A | N/A | N/A | 27.7 |
| | Freeze and thaw 10 times | colorless clear liquid | 6.40 | | 6.42×10$^{11}$ | 83.1 | N/A | N/A | N/A | 19.0 |
| | 40°C, 7days (illumination: 4500±500Lux) | colorless clear liquid | 6.40 | | 6.81×10$^{11}$ | 99.1 | N/A | N/A | N/A | 2.53 |
| 6 | T$_0$ | colorless clear liquid | 7.43 | 347 | 8.63×10$^{11}$ | 96.9 | N/A | N/A | N/A | 15.5 |
| | Freeze and thaw 10 times | colorless clear liquid | 7.45 | | 6.50×10$^{11}$ | 78.9 | N/A | N/A | N/A | 11.4 |
| | 40°C, 7days (illumination: 4500±500Lux) | colorless clear liquid | 7.46 | | 7.12×10$^{11}$ | 96.4 | N/A | N/A | N/A | 2.78 |

FIG. 1B

| Examples | Conditions | Appearance | pH | Osmotic pressure (mOsm/L) | qPCR (vg/ml) | SEC-HPLC (%) | 5μm insoluble particles (Cumulative Counts/ml) | 10μm insoluble particles (Cumulative Counts/ml) | 25μm insoluble particles (Cumulative Counts/ml) | in vitro activity hFIX expression (ng/ml) |
|---|---|---|---|---|---|---|---|---|---|---|
| 7 | T₀ | colorless clear liquid | 8.21 | 299 | $2.26 \times 10^{12}$ | 93.2 | N/A | N/A | N/A | 24.4 |
|  | Freeze and thaw 10 times | colorless clear liquid | 8.20 |  | $1.93 \times 10^{12}$ | 91.3 | N/A | N/A | N/A | 18.5 |
|  | 40°C, 7days (illumination:colorless 4500±500Lux) | colorless clear liquid | 8.19 |  | $2.23 \times 10^{12}$ | 94.5 | N/A | N/A | N/A | 10.2 |
| 8 | T₀ | colorless clear liquid | 8.09 | 373 | $2.17 \times 10^{12}$ | 95.1 | N/A | N/A | N/A | 13.6 |
|  | Freeze and thaw 10 times | colorless clear liquid | 8.09 |  | $2.20 \times 10^{12}$ | 96.4 | N/A | N/A | N/A | 8.9 |
|  | 40°C, 7days (illumination:colorless 4500±500Lux) | colorless clear liquid | 8.10 |  | $2.32 \times 10^{12}$ | 96.4 | N/A | N/A | N/A | 4.9 |
| 9 | T₀ | colorless clear liquid | 8.03 | 347 | $2.28 \times 10^{12}$ | 95.6 | N/A | N/A | N/A | 8.6 |
|  | Freeze and thaw 10 times | colorless clear liquid | 8.14 |  | $2.55 \times 10^{12}$ | 96.2 | N/A | N/A | N/A | 6.5 |
|  | 40°C, 7days (illumination:colorless 4500±500Lux) | colorless clear liquid | 8.10 |  | $2.48 \times 10^{12}$ | 94.7 | N/A | N/A | N/A | 3.9 |

FIG. 1C

| Examples | Conditions | Appearance | pH | Osmotic pressure (mOsm/L) | qPCR (vg/ml) | SEC-HPLC (%) | 5μm insoluble particles (Cumulative Counts/ml) | 10μm insoluble particles (Cumulative Counts/ml) | 25μm insoluble particles (Cumulative Counts/ml) | in vitro activity hFIX expression (ng/ml) |
|---|---|---|---|---|---|---|---|---|---|---|
| 10 | $T_0$ | colorless clear liquid | 8.23 | 370 | $9.33 \times 10^{11}$ | 95.8 | 70.0 | 10.0 | 0.0 | 26.7 |
| | Freeze and thaw 10 times | colorless clear liquid | 8.26 | | $9.22 \times 10^{11}$ | 96.3 | 140.0 | 17.5 | 0.0 | N/A |
| | 40°C, 7days (illumination: 4500±500Lux) | colorless clear liquid | 8.25 | | $1.10 \times 10^{12}$ | 95.5 | 92.5 | 15.0 | 0.0 | 20.3 |

FIG. 1D

| Detection item | | Acceptable standard | 0 Mon | 1 Mon | 2 Mon | 3 Mon | 6 Mon | 9 Mon | 12 Mon |
|---|---|---|---|---|---|---|---|---|---|
| Exterior | | Should be colorless clear liquid | meets the regulations | meets the regulations | meets the regulations | meets the regulations | meets the regulations | meets the regulations | meets the regulations |
| Clarity | | Not thicker than No. 3 turbidity standard solution | meets the regulations | meets the regulations | meets the regulations | meets the regulations | meets the regulations | meets the regulations | meets the regulations |
| Visible foreign matter | | Meets the regulations | meets the regulations | meets the regulations | meets the regulations | meets the regulations | meets the regulations | meets the regulations | meets the regulations |
| Poloxamer 188 (μg/ml) | | 30-150μg/ml | 90.6 | 94.0 | 79.6 | 76.7 | 80.4 | 72.0 | 79.2 |
| Osmolality (mOsmol/kg) | | 330–410 mOsmol/kg | 368 | N/A | N/A | N/A | 366 | N/A | N/A |
| Capacity (ml) | | Should not be less than the marked capacity | meets the regulations | N/A | N/A | N/A | meets the regulations | N/A | N/A |
| Purity (SDS-PAGE) | | The total purity of capsid protein should not be less than 95% | 100.0 | 100.0 | 100.0 | 100.0 | 100.00 | 100.1 | 100.0 |
| Purity (SEC-HPLC, %) | | Monomer purity should not be less than 95% | 98.0 | 97.4 | 96.1 | 96.0 | 99.5 | 98.6 | 99.9 |
| pH | | 7.7~8.3 | 7.8 | 7.8 | 7.9 | 7.9 | 7.9 | 7.8 | 7.8 |
| Number of viral particles (vp/ml) | | $4.0 \times 10^{12} \sim 9.0 \times 10^{12}$ vp/ml | $6.60 \times 10^{12}$ | $7.02 \times 10^{12}$ | $6.14 \times 10^{12}$ | $6.05 \times 10^{12}$ | $7.38 \times 10^{12}$ | $7.34 \times 10^{12}$ | $5.72 \times 10^{12}$ |
| Genome titer (vg/ml) | | $1.5 \times 10^{12} \sim 4.5 \times 10^{12}$ vg/ml | $2.81 \times 10^{12}$ | $2.85 \times 10^{12}$ | $2.69 \times 10^{12}$ | $3.08 \times 10^{12}$ | $3.00 \times 10^{12}$ | $2.67 \times 10^{12}$ | $2.60 \times 10^{12}$ |
| Activity in vitro | Relative activity (%) | Relative activity and relative content should be 50%~150% | 115.15 | 78.26 | 113.51 | 114.71 | 123.81 | 105.88 | 131.25 |
| | Relative content (%) | | 119.26 | 87.05 | 118.62 | 109.68 | 114.62 | 117.01 | 118.05 |

FIG. 2

PHARMACEUTICAL COMPOSITION OF A RECOMBINANT ADENO-ASSOCIATED VIRUS VECTOR AND ITS APPLICATION

CROSS-REFERENCE TO RELATED APPLICATIONS

This application claims the benefit of the Chinese application CN202211467932.8 filed on Nov. 22, 2022, the content of which is incorporated herein by reference in its entirety.

TECHNICAL FIELD

The disclosure belongs to the field of pharmaceutical formulations of recombinant adeno-associated virus vectors. The disclosure relates to a pharmaceutical composition of a recombinant adeno-associated virus vector and its application, in particular to a liquid formulation of a gene therapy drug with the recombinant adeno-associated virus as a vector and its application.

BACKGROUND

Cell and Gene Therapy (CGT) is a therapy to upgrade therapy or treat rare diseases. It overcomes the limitations of traditional small molecule and antibody drugs in protein level regulation through gene expression, silencing or in vitro modification. For CGT therapy, a very important part is the in vivo delivery of gene vectors. At present, common gene vectors are divided into non-viral vectors and viral vectors. Non-viral vectors include plasmids or naked DNA (non-viral), LNP delivery systems, etc., but the poor in vivo transfection effect and high toxicity seriously restrict the clinical transformation of non-viral vectors. Viral vectors include commonly used adenovirus (AdV), adeno-associated virus (AAV), lentivirus (LV), and retrovirus (RV).

Adeno-associated virus (AAV) was first identified in the mid-1960s from laboratory adenovirus (AdV) formulations and was quickly found in human tissues. Recombinant adeno-associated virus (rAAV) vectors usually replace the coding sequence of the virus with the interest gene. These vectors have been shown to have efficient expression and gene targeting at several different sites in vitro and in vivo. Studies have shown that AAV is safe and can be stably and continuously expressed in studies of the respiratory tract, central nervous system, skeletal muscle, liver and eyes. As the titer and purity of rAAV formulations increase, so does the efficiency of rAAV-mediated transduction.

At present, the number of rAAV-related clinical trials in the world is generally increasing. So far, four gene therapy products using rAAVs as vectors have been approved for marketing: In 2012, Glybera was approved by EMA for the treatment of lipoprotein lipase deficiency (LPLD), which is the first human AAV gene therapy product officially approved for marketing. At the end of 2017, the FDA approved Spark Therapeutics' Luxturna for the treatment of inherited retinal diseases, becoming the first "in vivo administration" gene therapy approved in the United States.

In May 2019, Novartis' Zolgensma was approved by the US FDA for the treatment of children with spinal muscular atrophy (SMA) under the age of 2 who have biallelic mutations in the survival motor neuron 1 (SMN1) gene.

On Aug. 24, 2022, BioMarin Pharmaceutical Inc. (BioMarin) announced that the European Commission (EC) approved the hemophilia A gene therapy ROCTAVIAN™ (valoctocogene roxaparvovec) conditional marketing, for the treatment of adult patients with severe hemophilia A who has no history of FVIII factor inhibitors and are AAV5 antibody negative.

The above gene therapy products need to be stored in a frozen state, and their transportation and storage temperatures are generally −20° C. or −60° C. Maintaining freezer temperatures at −20° C. or −60° C. is challenging and costly from a logistical standpoint. Such low temperature requirements can negatively impact the ability to distribute the product to a wide range of clinical sites. Therefore, it is desired to provide a pharmaceutical composition of a recombinant adeno-associated virus vector gene therapy drug that remains stable for more than 1 year under general refrigeration temperature conditions, so as to be suitable for transportation or clinical places to thaw and store the product in a freezer, until used for patient administration. In order to solve the above problems, the disclosure provides a pharmaceutical composition of a recombinant adeno-associated virus vector, especially a liquid formulation of a gene therapy drug using a recombinant adeno-associated virus as a vector. The pharmaceutical composition can be stored at a general refrigeration temperature, such as 2-8° C., for more than one year, and can keep indicators such as genome titer and biological activity stable, and it also has good stability when stored at room temperature for two weeks.

SUMMARY

The disclosure provides a pharmaceutical composition of a recombinant adeno-associated virus vector, comprising a recombinant adeno-associated virus (rAAV), an ionic salt, a buffer, a stabilizer and a surfactant, and the application thereof.

In some embodiments, the recombinant adeno-associated virus (rAAV) comprises one or more components from an adeno-associated virus serotype selected from the group consisting of AAV1, AAV2, AAV2tYF, AAV3, AAV4, AAV5, AAV6, AAV7, AAV8, AAV9, AAV10, AAV11, and AAVrh10. In some embodiments, the rAAV comprises a capsid protein of the AAV5 serotype.

In some embodiments, the ionic salt can be one or more components from the group consisting of sodium chloride, potassium chloride, magnesium chloride, calcium chloride, sodium sulfate, magnesium sulfate, calcium sulfate, and the hydrates thereof. In some embodiments, the buffer may be one or more components from the group consisting of potassium dihydrogen phosphate, potassium phosphate, disodium hydrogen phosphate, sodium dihydrogen phosphate, sodium phosphate hexahydrate, sodium dihydrogen phosphate monohydrate, tromethamine, tris(hydroxymethyl)aminomethane hydrochloride (Tris-HCl), amino acids, histidine, histidine hydrochloride (histidine-HCl), sodium succinate, sodium citrate, sodium acetate, and 4-(2-hydroxyethyl)-1-piperazineethanesulfonic acid (HEPES), sodium citrate, potassium citrate, and calcium citrate. In some embodiments, the stabilizer is one or more of sucrose, sorbitol, methionine, trehalose, mannose, mannitol, raffinose, lactitol, lactobionic acid, glucose, maltulose, isomaltulose, lactulose, maltose, lactose, isomaltose, maltitol, stachyose, melezitose, and dextran. In some embodiments, the surfactant is poloxamer and/or polysorbate (Tween), and the preferred surfactant is one or more of poloxamer 188, polysorbate 20, and polysorbate 80.

In some embodiments, the ionic salt can be present in the solution at a concentration of at least 0.5 mM, at least 5 mM, at least 10 mM, at least 20 mM, at least 30 mM, at least 50 mM, at least 100 mM, or at least 150 mM. In some embodiments, the ionic salt may be present in the solution at a concentration of 0.5-600 mM, or 1-300 mM, or 50-200 mM. In some embodiments, the ionic salt can be present in the solution at about 1 mM. In some embodiments, the ionic salt can be present in the solution at about 2 mM. In some embodiments, the ionic salt may be present in the solution at about 10 mM. In some embodiments, the ionic salt may be present in the solution at about 50 mM. In some embodiments, the ionic salt may be present in the solution at about 150 mM. In some embodiments, the ionic salt may be present in the solution at about 200 mM. In some embodiments, the ionic salt may be present in the solution at about 250 mM. In some embodiments, the buffer can be present in the solution at a concentration of at least 1 mM, at least 5 mM, at least 10 mM, or at least 20 mM. In some embodiments, the buffer may be present in the solution at 1-50 mM, or 5-30 mM, or 10-25 mM. In some embodiments, the buffer may be present in the solution at 10 mM. In some embodiments, the buffer can be present in the solution at about 12.5 mM. In some embodiments, the buffer can be present in the solution at about 15 mM. In some embodiments, the buffer may be present in the solution at about 17.5 mM. In some embodiments, the buffer can be present in the solution at about 20 mM. In some embodiments, the buffer can be present in the solution at about 22.5 mM. In some embodiments, the buffer can be present in the solution at about 25 mM.

In some embodiments, the stabilizer can be present in the solution at a concentration of at least 1 mM, at least 5 mM, at least 10 mM, at least 20 mM, at least 30 mM, at least 50 mM, at least 100 mM, or at least 200 mM. In some embodiments, the stabilizer may be present in the solution at a concentration of 10-500 mM, or 50-300 mM, or 100-250 mM. In some embodiments, the stabilizer may be present in the solution at a concentration of about 50 mM. In some embodiments, the stabilizer may be present in the solution at a concentration of about 100 mM. In some embodiments, the stabilizer may be present in the solution at a concentration of about 150 mM. In some embodiments, the stabilizer may be present in the solution at a concentration of about 200 mM. In some embodiments, the stabilizer may be present in the solution at a concentration of about 250 mM. In some embodiments, the stabilizer may be present in the solution at a concentration of about 300 mM.

In some embodiments, the surfactant may be present in the solution in a mass volume concentration (w/v) of at least 0.001%, at least 0.002%, at least 0.005%, or at least 0.01%. In some embodiments, the mass volume concentration of the surfactant may be 0.001%-0.1%, or 0.002%-0.05%, or 0.005%-0.02%. In some embodiments, the mass volume concentration of the surfactant may be 0.001%. In some embodiments, the mass volume concentration of the surfactant may be about 00.002%. In some embodiments, the mass volume concentration of the surfactant may be about 0.001%. In some embodiments, the mass volume concentration of the surfactant may be about 0.002%. In some embodiments, the mass volume concentration of the surfactant may be about 0.003%. In some embodiments, the mass volume concentration of the surfactant may be about 0.005%. In some embodiments, the mass volume concentration of the surfactant may be about 0.007%. In some embodiments, the mass volume concentration of the surfactant may be about 0.008%. In some embodiments, the mass volume concentration of the surfactant may be about 0.01%.

In some embodiments, the pH of the pharmaceutical composition is about 7.0-9.0. In some embodiments, the pH of the pharmaceutical composition is about 7.2-8.8. In some embodiments, the pH of the pharmaceutical composition is about 7.4-8.6. In some embodiments, the pH of the pharmaceutical composition is about 7.5-8.5. In some embodiments, the pH of the pharmaceutical composition is about 7.7-8.3. In some embodiments, the pH of the pharmaceutical composition is about 7.7. In some embodiments, the pH of the pharmaceutical composition is about 7.8. In some embodiments, the pH of the pharmaceutical composition is about 7.9. In some embodiments, the pH of the pharmaceutical composition is about 8.0. In some embodiments, the pH of the pharmaceutical composition is about 8.1. In some embodiments, the pH of the pharmaceutical composition is about 8.2. In some embodiments, the pH of the pharmaceutical composition is about 8.3. In some embodiments, the pH of the pharmaceutical composition is about 8.4. In some embodiments, the pH of the pharmaceutical composition is about 8.5. In some embodiments, the pH of the pharmaceutical composition is about 8.6.

Differential Scanning Fluorescence (DSF) as a Good Manufacturing Practice (GMP) application to be able to determine the melting temperature (Tm). AAV5 has a narrow range of Tm in different buffers. Vector stability is determined solely by VP3 of AAV, specifically the ratio of basic/acidic amino acids, and is independent of VP1 and VP2 content or the packaged genome. Furthermore, the stability of rAAV can be varied due to a single basic or acidic amino acid residue and can be distinguished. Comparative stability analysis of rAAV1-rAAV9 and rAAVrh. 10 in commonly used formulations and storage buffers revealed serotype-specific stability. A comparative analysis of rAAV in different buffers showed that each buffer had a different effect on each serotype, i.e., no buffer resulted in consistent stabilization or instabilization of all ten viruses tested (see Bennett, Antonette, et al. "Thermal stability as a determinant of AAV serotype identity." *Molecular Therapy—Methods & Clinical Development* 6 (2017): 171-182.).

In some embodiments, disclosed herein is a pharmaceutical composition of a recombinant adeno-associated virus vector, comprising a rAAV, an ionic salt, a buffer, a stabilizer, and a surfactant. The ionic salt is sodium chloride, potassium chloride. The buffer is tris(hydroxymethyl) aminomethane hydrochloride (Tris-HCl). The stabilizer is sucrose. The surfactant is Poloxamer 188. The pH of the pharmaceutical composition is about 7.0-9.0.

In some embodiments, disclosed herein is a pharmaceutical composition of a recombinant adeno-associated virus vector, comprising a rAAV, an ionic salt in an amount of 0.5-500 mM, a buffer in an amount of 1-50 mM, a stabilizer in an amount of 10-500 mM, and a surfactant in an amount of 0.001%-0.1% (w/v). The pH of the pharmaceutical composition is about 7.0-9.0. In some embodiments, disclosed herein is a pharmaceutical composition of a recombinant adeno-associated virus vector, comprising a rAAV, 1-500 mM sodium chloride, 0.1-100 mM magnesium chloride, 1-50 mM Tris-HCl, 10-500 mM sucrose or sorbitol, and 0.001%-0.1% (w/v) poloxamer 188. The pH of the pharmaceutical composition is about 7.0-9.0.

In some embodiments, disclosed herein is a pharmaceutical composition of a recombinant adeno-associated virus vector, comprising a rAAV, 10-300 mM sodium chloride, 0.5-5 mM magnesium chloride, 10-25 mM Tris-HCl, 50-300 mM sucrose or sorbitol, and 0.001%-0.01% (w/v) poloxamer 188. The pH of the pharmaceutical composition is about 7.5-8.5.

In some embodiments, disclosed herein is a pharmaceutical composition of a recombinant adeno-associated virus vector, characterized by comprising a rAAV, 1-500 mM sodium chloride, 0.1-100 mM magnesium chloride, 1-50 mM Tris-HCl, 10-500 mM sucrose or sorbitol, and 0.001%-0.1% (w/v) poloxamer 188, wherein the pH of the pharmaceutical composition is 7.0-9.0. Preferably, the concentration of the sodium chloride is 10-300 mM. Preferably, the concentration of the magnesium chloride is 0.5-5 mM. Preferably, the concentration of the Tris-HCl is 10-25 mM. Preferably, the concentration of the sucrose or sorbitol is 50-300 mM. Preferably, the concentration of the poloxamer 188 is 0.001%-0.01% (w/v). Preferably, the pH of the pharmaceutical composition is 7.6-8.6. More preferably, the concentration of sodium chloride is 100-150 mM; more preferably, the concentration of magnesium chloride is 1.0-1.5 mM; more preferably, the concentration of Tris-HCl is 20-25 mM; more preferably, the concentration of poloxamer 188 is 0.003%-0.005% (w/v). More preferably, the pH of the pharmaceutical composition is 8.2-8.6.

In some embodiments, the recombinant adeno-associated virus (rAAV) used herein carries human coagulation factor IX (hFIX), namely rAAV-hFIX. Coagulation factor IX is one of the main factors of the coagulation cascade, encoded by the FIX gene located on the X chromosome, and its loss-of-function mutation leads to hemophilia B (HB). Hemophilia B is a bleeding disorder caused by the deficiency of highly active coagulation factor IX. In severe patients, the activity of coagulation factor IX is often lower than 1% of that of the normal, and spontaneous bleeding often occurs, leading to muscle hematoma or joint deformity. Infusion of factor IX formulations (currently usually recombinantly expressed factor IX protein in vitro) to replenish the level of factor IX in patients is currently the only effective treatment, but frequent administration is required. Gene therapy is a treatment method currently undergoing clinical trials. The normal coagulation factor IX gene is introduced into the patient's body for long-term expression through a viral vector, so as to achieve the purpose of increasing the level of coagulation factor IX and preventing bleeding. It shall be noted that the sequence of human coagulation factor IX (hFIX) used herein is the sequence of highly active coagulation factor IX mutant (SEQ ID NO: 1) or the optimized coding sequence for coagulation factor IX expression (SEQ ID NO: 3) in the application with the application number CN201610898732.6 which was filed on Oct. 14, 2016, and the title "Preparation and application of high-activity blood coagulation factor IX mutant, recombinant protein and fusion protein". The sequence of the hFIX in the examples of the present application is the optimized coding sequence for coagulation factor IX expression (SEQ ID NO: 3), hFIX is only used as a model target gene introduced by the recombinant adeno-associated virus vector (rAAV) and the recombinant adeno-associated virus vector can also carry other suitable target genes for treating other corresponding diseases. In some embodiments, disclosed herein is a pharmaceutical composition of a recombinant adeno-associated virus vector, characterized in that it comprises a rAAV-hFIX, 1-500 mM sodium chloride, 0.1-100 mM magnesium chloride, 1-50 mM Tris-HCl, 10-500 mM sucrose or sorbitol, and 0.001%-0.1% (w/v) poloxamer 188, wherein the pH of the pharmaceutical composition is 7.0-9.0. The pharmaceutical composition of the recombinant adeno-associated virus vector can be used for treating hemophilia B. Preferably, the concentration of sodium chloride is 10-300 mM. Preferably, the concentration of magnesium chloride is 0.5-5 mM. Preferably, the concentration of Tris-HCl is 10-25 mM. Preferably, the concentration of sucrose or sorbitol is 50-300 mM. Preferably, the concentration of poloxamer 188 is 0.001%-0.01% (w/v). Preferably, the pH of the pharmaceutical composition is 7.6-8.6.

In some embodiments, disclosed herein is a pharmaceutical composition of a recombinant adeno-associated virus vector, comprising a rAAV-hFIX, 100-200 mM sodium chloride, 1.0-2.0 mM magnesium chloride, 15-25 mM Tris-HCl, 50-100 mM sucrose or sorbitol, and 0.001%-0.005% (w/v) poloxamer 188, wherein the pH of the pharmaceutical composition is 7.6-8.6. The pharmaceutical composition of the recombinant adeno-associated virus vector can be used for treating hemophilia B. Preferably, the concentration of sodium chloride is 100-150 mM. Preferably, the concentration of magnesium chloride is 1.0-1.5 mM. Preferably, the concentration of Tris-HCl is 20-25 mM. Preferably, the concentration of poloxamer 188 is 0.003%-0.005% (w/v). Preferably, the pH of the pharmaceutical composition is 8.2-8.6. In some embodiments, disclosed herein is a pharmaceutical composition of a recombinant adeno-associated virus vector, comprising a rAAV5, an ionic salt, a buffer, a stabilizer, and a surfactant. The ionic salt is sodium chloride, potassium chloride. The buffer is tris(hydroxymethyl) aminomethane hydrochloride (Tris-HCl). The stabilizer is sucrose. The surfactant is Poloxamer 188. The pH of the pharmaceutical composition is about 7.0-9.0. In some embodiments, disclosed herein is a pharmaceutical composition of a recombinant adeno-associated virus vector, comprising a rAAV5, an ionic salt in an amount of 0.5-500 mM, a buffer in an amount of 1-50 mM, a stabilizer in an amount of 10-500 mM, and a surfactant in an amount of 0.001%-0.1% (w/v). The pH of the pharmaceutical composition is about 7.0-9.0.

In some embodiments, disclosed herein is a pharmaceutical composition of a recombinant adeno-associated virus vector, comprising a rAAV5, 1-500 mM sodium chloride, 0.1-100 mM magnesium chloride, 1-50 mM Tris-HCl, 10-500 mM sucrose or sorbitol, and 0.001%-0.1% (w/v) poloxamer 188. The pH of the pharmaceutical composition is about 7.0-9.0.

In some embodiments, disclosed herein is a pharmaceutical composition of a recombinant adeno-associated virus vector, comprising a rAAV5, 10-300 mM sodium chloride, 0.5-5 mM magnesium chloride, 10-25 mM Tris-HCl, 50-300 mM sucrose or sorbitol, and 0.001%-0.01% (w/v) poloxamer 188. The pH of the pharmaceutical composition is about 7.5-8.5.

In some embodiments, the recombinant adeno-associated virus (rAAV) used herein carries human coagulation factor IX (hFIX), namely rAAV-hFIX, preferably rAAV5-hFIX. Coagulation factor IX is one of the main factors of the coagulation cascade, encoded by the FIX gene located on the X chromosome, and its loss-of-function mutation leads to hemophilia B (HB). Hemophilia B is a bleeding disorder caused by the deficiency of highly active coagulation factor IX. In severe patients, the activity of coagulation factor IX is often lower than 1% of that of the normal, and spontaneous bleeding often occurs, leading to muscle hematoma or joint deformity. Infusion of factor IX formulations (currently usually recombinantly expressed factor IX protein in vitro) to replenish the level of factor IX in patients is currently the only effective treatment, but frequent administration is required. Gene therapy is a treatment method currently undergoing clinical trials. The normal coagulation factor IX gene is introduced into the patient's body for long-term expression through a viral vector, so as to achieve the purpose of increasing the level of coagulation factor IX and preventing bleeding. It should be noted that the sequence of human coagulation factor IX (hFIX) used herein is the sequence of highly active coagulation factor IX mutant (SEQ ID NO: 1) or the optimized coding sequence for coagulation factor IX expression (SEQ ID NO: 3) in the application with the application number CN201610898732.6 which was filed on Oct. 14, 2016, and the title "Preparation and application of high-activity blood coagulation factor IX mutant, recombinant protein and fusion protein". The sequence of hFIX in the examples of the present application is the optimized coding sequence for coagulation factor IX expression (SEQ ID NO: 3), hFIX is only used as a model target gene introduced by the recombinant adeno-associated virus vector (rAAV), and the recombinant adeno-associated virus vector can also carry other suitable target genes for treating other corresponding diseases. The pharmaceutical composition as described herein may comprise one or more recombinant vectors capable of inducing an immune response, such as a humoral (e.g., antibody) response and/or a cell-mediated (e.g., cytotoxic T cell) response against the genes delivered by the vectors after administered to mammals (suitable human beings). The recombinant adeno-associated virus may contain (suitably in any of its gene deletions) a gene encoding a desired immunogen, and thus may be used in a vaccine. Recombinant adeno-associated virus can be used as a prophylactic or therapeutic vaccine against any pathogen for which an antigen critical for the induction of an immune response and able to limit the spread of the pathogen has been identified and its cDNA is available.

In some embodiments, disclosed herein is a pharmaceutical composition of a recombinant adeno-associated virus vector, characterized by comprising a rAAV5, 1-500 mM sodium chloride, 0.1-100 mM magnesium chloride, 1-50 mM Tris-HCl, 10-500 mM sucrose or sorbitol, and 0.001%-0.1% (w/v) poloxamer 188, wherein the pH of the pharmaceutical composition is 7.0-9.0. Preferably, the concentration of sodium chloride is 10-300 mM. Preferably, the concentration of magnesium chloride is 0.5-5 mM. Preferably, the concentration of Tris-HCl is 10-25 mM. Preferably, the concentration of sucrose or sorbitol is 50-300 mM. Preferably, the concentration of poloxamer 188 is 0.001%-0.01% (w/v). Preferably, the pH of the pharmaceutical composition is 7.6-8.6. More preferably, the concentration of sodium chloride is 100-150 mM; more preferably, the concentration of magnesium chloride is 1.0-1.5 mM; more preferably, the concentration of Tris-HCl is 20-25 mM; more preferably, the concentration of poloxamer 188 is 0.003%-0.005% (w/v). More preferably, the pH of the pharmaceutical composition is 8.2-8.6.

In some embodiments, disclosed herein is a pharmaceutical composition of a recombinant adeno-associated virus vector, characterized in that it comprises a rAAV5-hFIX, 1-500 mM sodium chloride, 0.1-100 mM magnesium chloride, 1-50 mM Tris-HCl, 10-500 mM sucrose or sorbitol, and 0.001%-0.1% (w/v) poloxamer 188, wherein the pH of the pharmaceutical composition is 7.0-9.0. The pharmaceutical composition of the recombinant adeno-associated virus vector can be used for treating hemophilia B. Preferably, the concentration of sodium chloride is 10-300 mM. Preferably, the concentration of magnesium chloride is 0.5-5 mM. Preferably, the concentration of Tris-HCl is 10-25 mM. Preferably, the concentration of sucrose or sorbitol is 50-300 mM. Preferably, the concentration of poloxamer 188 is 0.001%-0.01% (w/v). Preferably, the pH of the pharmaceutical composition is 7.6-8.6.

In some embodiments, disclosed herein is a pharmaceutical composition of a recombinant adeno-associated virus vector, comprising a rAAV5-hFIX, 100-200 mM sodium chloride, 1.0-2.0 mM magnesium chloride, 15-25 mM Tris-HCl, 50-100 mM sucrose or sorbitol, and 0.001%-0.005% (w/v) poloxamer 188, wherein the pH of the pharmaceutical composition is 7.6-8.6. The pharmaceutical composition of the recombinant adeno-associated virus vector can be used for treating hemophilia B. Preferably, the concentration of sodium chloride is 100-150 mM. Preferably, the concentration of magnesium chloride is 1.0-1.5 mM. Preferably, the concentration of Tris-HCl is 20-25 mM. Preferably, the concentration of poloxamer 188 is 0.003%-0.005% (w/v). Preferably, the pH of the pharmaceutical composition is 8.2-8.6.

In some embodiments, the compositions described herein are used in the immunization of a subject (e.g., a human). Immunity levels of selected genes can be monitored to determine if a boosting is needed. Following assessment of antibody titers in sera, optional booster immunizations may be desired.

Optionally, the compositions of the present invention can be formulated to contain other components, including pharmaceutically acceptable vectors, e.g., adjuvants, preservatives and the like.

In certain embodiments, a composition as described herein is administered to the subject via intramuscular injection, intravaginal administration, intravenous injection, intraperitoneal injection, subcutaneous injection, intradermal administration, intradermal administration, nasal administration, or oral administration.

If the treatment regimen comprises co-administration of one or more adeno-associated viral vectors and/or other components, these may be co-formulated (i.e., in the same mixture or composition) or separately formulated in different compositions. When formulated separately, they are advantageously administered co-located at or near the same site. For example, the components may be administered to the same limb (e.g., intramuscularly, transdermally, intradermally, subcutaneously) ("ipsilateral" administration) or to the opposite limb ("contralateral" administration).

The dosage of the viral vector depends primarily on factors such as the condition being treated, the age, weight and health of the patient, and thus may vary from patient to patient. For example, a therapeutically effective adult or veterinary dose of a viral vector typically contains $1 \times 10^5$ to $1 \times 10^{15}$ viral particles, such as $1 \times 10^8$-$1 \times 10^{13}$ (e.g., $1 \times 10^8$, $1 \times 10^9$, $1 \times 10^{10}$, $1 \times 10^{11}$, $1 \times 10^{12}$, $1 \times 10^{13}$ particles). Alternatively, the viral vector can be typically administered in a dose of a genome titer (vg/ml) of $1 \times 10^8$-$1 \times 10^{13}$, e.g., $1 \times 10^8$ vg/ml, $1 \times 10^9$ vg/ml, $1 \times 10^{10}$ vg/ml, $1 \times 10^{11}$ vg/ml, $1 \times 10^{12}$ vg/ml or $1 \times 10^{13}$ vg/ml. Dosages can vary depending on the size of the animal and the route of administration. For example, a suitable human or veterinary dose for intramuscular injection (for an animal of about 80 kg) is in the range of about $1 \times 10^9$ to about $5 \times 10^{12}$ particles/mL for a single site. Optionally, multiple administration sites can be used. In some embodiments, suitable human or veterinary dosages may be in the range of about $1 \times 10^{11}$ to about $1 \times 10^{15}$ particles/mL for oral formulations.

In order to develop a formulation for the long-term stable storage of a liquid formulation of the recombinant adeno-associated virus vector, and ensure the quality of the product within the validity period (tentatively 24 months), the studies on formulation such as pH screening, excipient screening, and surfactant screening were carried out. The final formulation of the recombinant adeno-associated virus vector liquid formulation was determined. According to the literatures, the virus is prone to aggregation, has a larger particle size, and easy to be inactivated at high temperature after repeated freezing and thawing. The formulation screening process uses repeated freezing and thawing, high temperatures at 25° C. or 40° C. and other investigation conditions to accelerate the changes in the physical and biochemical properties of the virus in each formulation, thereby screening out the most stable formulations.

The characterization of the stability of the pharmaceutical composition of the recombinant adeno-associated virus vector can be determined by observing or detecting the appearance clarity, osmotic pressure, fluorescent quantitative PCR, size exclusion chromatography-high performance liquid chromatography (SEC-HPLC), dodecyl sulfate sodium polyacrylamide gel electrophoresis (SDS-PAGE), the number of insoluble particles, and in vitro activity (expressed by the expression of hFIX).

Fluorescent quantitative polymerase chain reaction analysis (qPCR) is a method of measuring the total amount of products after each cycle of polymerase chain reaction (PCR) with fluorescent chemicals in DNA amplification induction, which is a method for quantitative analysis of a specific DNA sequence in a test sample through internal reference or external reference method. qPCR can quantify adeno-associated viral vectors.

Insoluble particles can be measured using a microscope insoluble particle detector.

Size exclusion chromatography-high performance liquid chromatography (SEC-HPLC) detects the purity of the pharmaceutical composition of the recombinant adeno-associated virus vector. Sodium dodecyl sulfate polyacrylamide gel electrophoresis (SDS-PAGE) is the most commonly used protein expression analysis technique in polyacrylamide gel electrophoresis. The principle of this technique is to separate proteins in electrophoresis gels according to different molecular weights of the proteins in the sample. SDS-PAGE is usually used to detect protein expression (expression amount, expression distribution), and analyze the purity of target proteins.

The expression amount of active hFIX in vitro is to measure the protein content of hFIX in the pharmaceutical composition of the recombinant adeno-associated virus vector by double-antibody sandwich ELISA method. A specific antibody (i.e., primary antibody, capture antibody) is used to coat a solid-phase carrier to form a solid-phase antibody, after blocking and washing, a sample to be tested is added, and after incubation and washing a biotin-labeled antibody (i.e., secondary antibody, detection antibody) is added. After incubation and washing, streptavidin-peroxide (SA-HRP) is added, after incubation and washing, a chromogenic substrate is added for determination, and the protein content of hFIX in the sample to be tested is obtained by colorimetry.

DESCRIPTION OF DRAWINGS

FIGS. 1A, 1B, 1C and 1D show the experimental results of Examples 1-10, wherein N/A means not available, or not tested.

FIG. 2 shows the experimental results of the long-term stability investigation of the liquid formulation of the recombinant adeno-associated virus vectors in Examples 1-10 placed at 2-8° C.

DETAILED DESCRIPTION

Below in conjunction with specific examples, the present invention is further illustrated. It should be understood that these examples are only used to illustrate the present invention and are not intended to limit the scope of the present invention. In addition, it should be understood that after reading the disclosure of the present invention, those skilled in the art may make various changes or modifications to the present invention, and these equivalents also fall within the scope defined by the appended claims of the present application.

Example 1

A liquid formulation of recombinant adeno-associated virus vector comprised rAAV5-hFIX, 100 mM sodium chloride, 1.5 mM magnesium chloride, 15 mM Tris-HCl, 50 mM sucrose, and 0.003% (w/v) poloxamer 188. The pH of the formulation was 7.6.

Example 2

A liquid formulation of recombinant adeno-associated virus vector comprised rAAV5-hFIX, 150 mM sodium chloride, 1.0 mM magnesium chloride, 20 mM Tris-HCl, 50 mM sucrose, and 0.005% (w/v) poloxamer 188. The pH of the formulation was 8.2.

Example 3

A liquid formulation of recombinant adeno-associated virus vector comprised rAAV5-hFIX, 200 mM sodium chloride, 2.0 mM magnesium chloride, 25 mM Tris-HCl, 100 mM sucrose, and 0.001% (w/v) poloxamer 188. The pH of the formulation was 8.6.

Example 4

A liquid formulation of recombinant adeno-associated virus vector comprised rAAV5-hFIX, 150 mM sodium chloride, 1.0 mM magnesium chloride, 20 mM Tris-HCl, 50 mM sorbitol, and 0.005% (w/v) poloxamer 188, and the pH of the formulation was 8.2.

Example 5

A liquid formulation of recombinant adeno-associated virus vector comprised rAAV5-hFIX, 200 mM sodium chloride, 1.0 mM magnesium chloride, 10 mM disodium hydrogen phosphate/sodium dihydrogen phosphate, 50 mM sucrose, and 0.005% (w/v) Poloxamer 188. The pH of the formulation was 6.5.

Example 6

A liquid formulation of recombinant adeno-associated virus vector comprised rAAV5-hFIX, 200 mM sodium chloride, 1.0 mM magnesium chloride, 10 mM disodium hydrogen phosphate/sodium dihydrogen phosphate, 50 mM sucrose, and 0.005% (w/v) The poloxamer 188. The pH of the formulation was 7.5.

Example 7

A liquid formulation of recombinant adeno-associated virus vector comprised rAAV5-hFIX, 150 mM sodium chloride, 1.0 mM magnesium chloride, 20 mM Tris-HCl, and 0.005% (w/v) poloxamer 188. The pH of the formulation was 8.2.

Example 8

A liquid formulation of recombinant adeno-associated virus vector comprised rAAV5-hFIX, 150 mM sodium chloride, 10 mM magnesium chloride, 20 mM Tris-HCl, 50 mM sucrose, and 0.005% (w/v) poloxamer 188. The pH of the formulation was 8.2.

Example 9

A liquid formulation of recombinant adeno-associated virus vector comprised rAAV5-hFIX, 150 mM sodium chloride, 1.0 mM methionine, 20 mM Tris-HCl, 50 mM sucrose, and 0.005% (w/v) poloxamer 188. The pH of the formulation was 8.2.

Example 10

A liquid formulation of recombinant adeno-associated virus vector comprised rAAV5-hFIX, 150 mM sodium chloride, 1.0 mM magnesium chloride, 20 mM Tris-HCl, 50 mM sucrose, and 0.005% (w/v) polysorbate 80. The pH of the formulation was 8.2.

The experimental results of the stability investigation of Examples 1-10 are shown in FIGS. 1A, 1B, 1C and 1D, wherein the liquid formulations of the recombinant adeno-associated virus vectors of Examples 1-4 had better stability and less insoluble particles. And the expression of active hFIX in vitro was the highest. Compared with the liquid preparation of Example 2, the pH of the liquid preparation of Example 5 was 6.5, and the SEC-HPLC data of Example 5 showed reduced purity, and reduced expression of in vitro active hFIX. Compared with the liquid formulation of Example 1, the pH value of the liquid formulation of Example 5 was close, but different buffer, disodium hydrogen phosphate/sodium dihydrogen phosphate was used, and its SEC-HPLC data showed reduced purity, and reduced expression of in vitro active hFIX. Compared with the liquid preparation of Example 2, the liquid preparation of Example 7 did not contain sucrose as a stabilizer, and the SEC-HPLC data of Example 7 showed that its purity was slightly lower, and the expression level of in vitro active hFIX was also lower. Compared with the liquid formulation of Example 2, the concentration of magnesium chloride was increased to 10 mM in the liquid formulation of Example 8, and the SEC-HPLC data of Example 8 showed that its purity was slightly lower, and the expression of active hFIX in vitro also decreased. Compared with the liquid preparation of Example 2, magnesium chloride was replaced with methionine in the liquid preparation of Example 9, and the SEC-HPLC data of Example 9 showed that its purity was slightly lower, and the expression level of in vitro active hFIX was also lower. Compared with the liquid preparation of Example 2, magnesium chloride was replaced with methionine in the liquid preparation of Example 10, and the SEC-HPLC data of Example 10 showed that its purity was slightly lower, and the expression level of in vitro active hFIX was also lower.

Example 11

For long-term stability test, the liquid preparation of the recombinant adeno-associated virus vector in Example 2 was placed at 2-8° C., and the key indicators such as in vitro activity and genome titer of the product were measured after 0, 1, 2, 3, 6, 9 and 12 months, which did not have a significant downward trend, indicating that the liquid preparation of the recombinant adeno-associated virus vector in Example 2 can remain stable for a long time at 2-8° C., and is more advantageous than current storage conditions that need to be stored in frozen storage, making it convenient for product transportation and clinical use, and reducing the investment and use costs of all relevant parties.

Unless defined otherwise, all technical and scientific terms used herein have the same meanings as commonly understood by one of ordinary skill in the art to which this invention belongs. Although any methods and materials similar or equivalent to those described herein can be used in the practice of testing of the present invention, the preferred materials and methods are described herein. In describing and claiming the present invention, the following technical term will be used.

It is also to be understood that the technical term used herein is for the purpose of describing particular embodiments only and is not intended to be limiting.

As used herein, when referring to a measurable value such as an amount, duration of time, etc., the term "about" is meant to include ±20% or ±10%, more preferably ±5%, even more preferably ±1%, and still more preferably ±0.1% variations from the stated value, whereby these variations are suitable for carrying out the disclosed methods.

As used herein, the term "pharmaceutical composition" refers to a mixture of at least one active ingredient useful in the present invention with other chemical components such as carriers, stabilizers, diluents, adjuvants, dispersants, suspending agents, thickeners and/or excipients. Pharmaceutical compositions facilitate the administration of active ingredients to an organism. Various techniques for administering compounds exist in the art including, but not limited to, intravenous, oral, aerosol, parenteral, intraocular, pulmonary, and topical administration.

As used herein, the term "pharmaceutically acceptable carrier" includes pharmaceutically acceptable salts, pharmaceutically acceptable materials, compositions or vehicles, such as liquid or solid fillers, diluents, excipients, solvents or an encapsulating material that participates in the delivery or transport of the compound(s) of the invention within or to a subject so that it can perform its intended function. Typically, such compounds are transported or transported from one organ or part of the body to another organ or part of the body. Each salt or carrier must be "acceptable" in the sense of being compatible with the other ingredients of the formulation and not injurious to the subject. Some examples of materials that can be used as pharmaceutically acceptable carriers include: sugars, such as lactose, glucose, and sucrose; starches, such as corn starch and potato starch; cellulose and its derivatives, such as sodium carboxymethylcellulose, ethyl cellulose and cellulose acetate; tragacanth powder; malt; gelatin; talc; excipients such as cocoa butter and suppository waxes; oils such as peanut oil, cottonseed oil, safflower oil, sesame oil, olive oil, corn oils and soybean oils; glycols, such as propylene glycol; polyols, such as glycerin, sorbitol, mannitol, and polyethylene glycol; esters, such as ethyl oleate and ethyl laurate; agar; buffers, such as magnesium hydroxide and aluminum hydroxide; alginic acid; pyrogen-free water; isotonic saline; Ringer's solution; ethanol; phosphate buffer solution; diluents; granulating agents; lubricants; binders; disintegrants; wetting agents; emulsifiers; colorants; release agents; coating agents; sweeteners; seasonings; flavoring agents; preservatives; antioxidants; plasticizers; gelling agents; thickeners; hardeners; sedimentation agents; suspending agents; surfactants; humectants; carriers; stabilizers; and other nontoxic compatible substances used in pharmaceutical formulations, or any combination thereof. As used herein, "pharmaceutically acceptable carrier" also includes any and all coatings, antibacterial and antifungal agents, and absorbing delay agents, and the like that are compatible with the activity of the compound and are physiologically acceptable to the subject. Supplementary active compounds can also be incorporated into the compositions.

While the invention has been described in detail with reference to specific examples thereof, it should be understood that functionally equivalent changes are within the scope of the invention. Indeed, various modifications of the invention in addition to those shown and described herein will become apparent to those skilled in the art from the foregoing description and accompanying drawings. Those skilled in the art will recognize, or be able to ascertain using no more than routine experimentation, many equivalents to the specific embodiments of the invention described herein.

All publications, patents, and patent applications mentioned in this specification are hereby incorporated by reference into this specification to the same extent as if each individual publication, patent, or patent application was specifically and individually indicated to be incorporated by reference in its entirety.

The invention claimed is:

1. A pharmaceutical composition of a recombinant adeno-associated virus (rAAV) vector comprising: (a) a rAAV, (b) sodium chloride, (c) magnesium chloride, (d) Tris-HCl, (e) sucrose or sorbitol, and (f) Poloxamer 188, wherein the rAAV is rAAV5, the pH of the pharmaceutical composition is 7.6-8.6, the concentration of sodium chloride is 100-200 mM, the concentration of magnesium chloride is 1.0-2.0 mM, the concentration of Tris-HCl is 15-25 mM, the concentration of sucrose or sorbitol is 50-100 mM, and the concentration of Poloxamer 188 is 0.001%-0.005% (w/v), and wherein the composition is stable for 12 months.

2. The pharmaceutical composition of the rAAV vector of claim 1, wherein the concentration of sodium chloride is 100-150 mM.

3. The pharmaceutical composition of the rAAV vector of claim 1, wherein the concentration of magnesium chloride is 1.0-1.5 mM.

4. The pharmaceutical composition of the rAAV vector of claim 1, wherein the concentration of Tris-HCl is 20-25 mM.

5. The pharmaceutical composition of the rAAV vector of claim 1, wherein the concentration of Poloxamer 188 is 0.003%-0.005% (w/v).

6. The pharmaceutical composition of the rAAV vector of claim 1, wherein the pH of the pharmaceutical composition is 8.2-8.6.

7. A pharmaceutical composition of a recombinant adeno-associated virus (rAAV) vector comprising: (a) a rAAV-hFIX, (b) sodium chloride, (c) magnesium chloride, (d) Tris-HCl, (e) sucrose or sorbitol, and (f) Poloxamer 188, wherein the rAAV is rAAV5, the pH of the pharmaceutical composition is 7.6-8.6, the concentration of sodium chloride is 100-200 mM, the concentration of magnesium chloride is 1.0-2.0 mM, the concentration of Tris-HCl is 15-25 mM, the concentration of sucrose or sorbitol is 50-100 mM, and the concentration of Poloxamer 188 is 0.001%-0.005% (w/v), and wherein the composition is stable for 12 months.

8. The pharmaceutical composition of the rAAV vector of claim 7, wherein the concentration of sodium chloride is 100-150 mM.

9. The pharmaceutical composition of the rAAV vector of claim 7, wherein the concentration of magnesium chloride is 1.0-1.5 mM.

10. The pharmaceutical composition of the rAAV vector of claim 7, wherein the concentration of Tris-HCl is 20-25 mM.

11. The pharmaceutical composition of the rAAV vector of claim 7, wherein the concentration of Poloxamer 188 is 0.003%-0.005% (w/v).

12. The pharmaceutical composition of the rAAV vector of claim 7, wherein the pH of the pharmaceutical composition is 8.2-8.6.

* * * * *